United States Patent
Waddell et al.

(10) Patent No.: US 7,601,347 B2
(45) Date of Patent: Oct. 13, 2009

(54) METHODS AND COMPOSITIONS FOR CONTROLLED RELEASE OF BIOACTIVE COMPOUNDS

(76) Inventors: Thomas E. Waddell, 1795 Brock Road, Freelton Ontario (CA) L0R 1K0; Roger Johnson, 36 Glassgrow Street North, Guelph Ontario (CA) N1H 4V5; Amanda Mazzocco, 2 Valeriote Place, Guelph Ontario (CA)

( * ) Notice: Subject to any disclaimer, the term of this patent is extended or adjusted under 35 U.S.C. 154(b) by 216 days.

(21) Appl. No.: 10/819,925

(22) Filed: Apr. 8, 2004

(65) Prior Publication Data

US 2004/0208854 A1    Oct. 21, 2004

Related U.S. Application Data

(60) Provisional application No. 60/463,319, filed on Apr. 17, 2003.

(51) Int. Cl.
  *A61K 45/00* (2006.01)
  *A61K 9/20* (2006.01)
(52) U.S. Cl. .................... 424/93.6; 424/465; 514/53
(58) Field of Classification Search .................. None
  See application file for complete search history.

(56) References Cited

U.S. PATENT DOCUMENTS 6,485,902 B2 * 11/2002 Waddell et al. ................ 435/5
2004/0018236 A1 * 1/2004 Gurny et al. ................ 424/471

* cited by examiner

*Primary Examiner*—Robert A Zeman
(74) *Attorney, Agent, or Firm*—Michael R. Williams; Ade & Company Inc.

(57) ABSTRACT

A controlled release pharmaceutical dosage form for bacteriophage is presented. The dosage form is prepared by drying the active ingredient together with a dispersion or solution of polymethacrylate copolymer and a lyprotectant using mild, entirely aqueous conditions.

7 Claims, No Drawings

METHODS AND COMPOSITIONS FOR CONTROLLED RELEASE OF BIOACTIVE COMPOUNDS

PRIOR APPLICATION INFORMATION

This application claims priority on U.S. Ser. No. 60/463,319, filed Apr. 17, 2003.

FIELD OF THE INVENTION

The present invention relates generally to the field of drug delivery.

BACKGROUND OF THE INVENTION

Bacterial infections in carrier animals by human pathogens, such as *Escherichia coli* O157:H7, *Campylobacter* spp., and *Salmonella* spp., etc, may be controlled by bacteriophages that attack and kill these bacteria. In order for enteric infections to be controlled with bacteriophages the bacteriophages must be given to animals by mouth in a form that will allow them to act at the site of infection, typically distal to the stomach. Bacteriophage have properties that make preparation of suitable dosage forms difficult. For example, bacteriophages are typically damaged irreversibly by exposure to harsh conditions, by conventional drying techniques and by low pH and proteolysis in the stomach and in the gastrointestinal tract. This damage results from pH-dependent denaturation and proteolytic degration of proteins vital to the viability of the bacteriophage. Bacteriophage represent extremely complicated therapeutics since they are comprised of DNA, or RNA and proteins. Frequently, bacteriophages contain elaborate receptor-binding tail structures that are particularly sensitive to breakage. In essence, our ability to exploit the therapeutic potential of bacteriophages is severely limited by the sensitivity of bacteriophages to low pH, proteolytic degradation and denaturation due to drying, and the lack of suitable methods for preparing economical and effective solid dosage forms.

The therapeutic potential of bacteriophage is described in various reports. In these studies the bacteriophage were used in aqueous form with or without buffers to neutralize stomach acid. These formulations are not ideal because they lack practicality. No methods to produce stabilized, controlled release dosage formulations of bacteriophage have been described.

A bacteriophage delivery system is needed deliver bacteriophage in a controlled manner to enable commercial development of the agents.

Methacrylic acid copolymers (EUDRAGITS™ (methacrylic acid-methyl methacrylate copolymers) have been used extensively to prepare controlled release oral dosage forms of drugs. These polymers have great utility for this purpose because they have been engineered to become soluble in different pH environments. For example, EUDRAGIT (methacrylic acid-methyl methacrylate copolymer) L100 dissolves above pH 5.5 and will protect an active ingredient in acid environments, such as the stomach, yet upon exposure to neutral or basic environments the same dosage form will release the active ingredient. In this regard, the aqueous solubility of the methacrylic acid copolymers is controlled by the degree of protonation of carboxyl groups, which are present on the polymer backbone. If the carboxyl groups are deprotonated, as occurs in basic or neutral environments, the resulting ionic carboxylate groups increase the aqueous solubility of the polymer.

Methacrylic acid copolymers are typically applied to drug-containing cores as thin layers by ladling or spray coating. Alternatively, they may be incorporated into monolithic matrix devices by compression techniques, or by other techniques, such as spray drying. Methacrylic acid copolymers are used generally in the protonated form, either as aqueous dispersions under low pH conditions, or as solutions in organic solvents. Using these conditions has a number of drawbacks. For example, the physical characteristics of the material in dispersion may be detrimental to the drug activity, particularly when it is a biological macromolecule. Similarly, the activity of the drug may be adversely affected by exposure to organic solvents.

Methacrylic acid copolymers have not been used to coat bacteriophages for enteric delivery.

SUMMARY OF THE INVENTION

According to a first aspect of the invention, there is provided a pharmaceutical composition comprising:
  a methacrylic acid polymer solution or dispersion;
  a lyoprotectant; and
  a bioactive agent.

According to a second aspect of the invention, there is provided a method of preparing a pharmaceutical composition comprising:
  mixing a methacrylate polymer and water;
  adding a lyoprotectant and a bioactive agent to the mixture; and
  drying the mixture.

According to a third aspect of the invention, there is provided a method of treating a bacterial infection comprising:
  administering to an animal in need of such treatment a therapeutic amount of a dried pharmaceutical composition comprising:
  a methacrylic acid polymer;
  a lyoprotectant; and
  a bacteriophage.

According to a fourth aspect of the invention, there is provided a method of treating a bacterial infection comprising:
  administering to an animal in need of such treatment a therapeutic amount of a dried pharmaceutical composition comprising:
  a methacrylic acid polymer;
  a lyoprotectant; and
  a bioactive agent.

According to a fifth aspect of the invention, there is provided a method of treating a disease condition comprising:
  administering to an animal in need of such treatment a therapeutic amount of a dried pharmaceutical composition comprising:
  a methacrylic acid polymer;
  a lyoprotectant; and
  a bioactive agent.

BRIEF DESCRIPTION OF THE TABLES

Table 1. Viability of rV5 in formulations containing a) polymethacrylate copolymer (EUDRAGIT (methacrylic acid-methyl methacrylate copolymer) L100), b) sucrose, and c) polymethacrylate copolymer (EUDRAGIT (methacrylic acid-methyl methacrylate copolymer) L100) and sucrose.

Table 2. Viability of rV5 in formulations containing a) polymethacrylate copolymer (EUDRAGIT (methacrylic acid-methyl methacrylate copolymer) L100), b) sucrose, and c)

polymethacrylate copolymer (EUDRAGIT (methacrylic acid-methyl methacrylate copolymer) L100) and sucrose.

Table 3. Protection of rV5 to acid treatment for 20 minutes by formulations containing a) polymethacrylate copolymer (EUDRAGIT (methacrylic acid-methyl methacrylate copolymer) L100), b) sucrose, and c) polymethacrylate copolymer (EUDRAGIT (methacrylic acid-methyl methacrylate copolymer) L100) and sucrose.

Table 4. Protection of rV5 to acid treatment overnight by formulations containing a) polymethacrylate copolymer (EUDRAGIT (methacrylic acid-methyl methacrylate copolymer) L100), b) sucrose, and c) polymethacrylate copolymer (EUDRAGIT (methacrylic acid-methyl methacrylate copolymer) L100) and sucrose.

Table 5. Controlled release of bacteriophage rV5 from formulation made using excipient containing 5% sucrose and 10% polymethacrylate S100.

Table 6. Controlled release of bacteriophage rV5 from formulation made using excipient containing 5% sucrose and 5% polymethacrylate S100.

Table 7. Controlled release of bacteriophage rV5 and wV8 from formulations containing polymethacrylate copolymer (EUDRAGIT (methacrylic acid-methyl methacrylate copolymer) S100) and sucrose.

Table 8. Rapid release of rV5 and wV8 from formulations containing polymethacrylate copolymer (EUDRAGIT (methacrylic acid-methyl methacrylate copolymer) S100) and sucrose.

Table 9. Viability of bacteriophage rV5 in formulations containing polymethacrylate copolymer (EUDRAGIT (methacrylic acid-methyl methacrylate copolymer) S100) and sucrose prepared by spray drying.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

As used herein, "bioactive compound" or "bioactive agent" refers to compounds having a biological effect. Examples include but are by no means limited to bacteriophage, pharmaceutical compounds, antibodies, receptor ligands, viruses, peptides, peptide fragments and the like.

As used herein, "animals" refers to vertebrates and invertebrates.

As used herein, "enteropathic organism" refers to an organism capable of colonizing the gastrointestinal tract of an animal. Examples of enterotoxigenic microogranisms include but are by no means limited to *Bacillus cereus, Bacillus anthracis, Bacillus subtilis, Bacillus thuringiensis, Bacillus stearothermophilus, Vibrio parahemolyticus, Vibrio cholerae* O1, *Vibrio cholerae* non-O1, *Vibrio vulnificus, Salmonella enterica, Salmonella typhi, Salmonella paratyphi, Salmonella entertidis, Salmonella cholerasuis, Salmonella typhimurium, Clostridium difficile, Clostridium botulinum, Clostridium perfringens, Staphylococcus aureus, Escherichia coli* (ETEC, EPEC, EHEC, EaggEC, UPEC and EIEC), *Campylobacter jejuni, Campylobacter coli, Campylobacter lari, Campylobacter fetus, Yersinia enterocolitica, Yersinia pestis, Yersinia pseudotuberculosis, Listeria monocytogenes, Shigella, Streptococcus, Actinobacillus, Lactobacillus, Citrobacter*, and *Pseudomonas aeruginosa.*

As used herein, "effective amount" refers to a dosage sufficient to have the desired effect.

Enterotoxigenic microorganisms cause a number of diseases and disorders, including, for example, dysentery, gastroenteritis, typhoid fever, cholera, infectious hepatitis, poliomyelitis and diarrhea. Typically, normal motor propulsive activity, mucosal immunity and other factors limit the growth of organisms in the small intestine. However, when the stress of excess pathogens and toxins is too overwhelming for the mucosal immune system, enterotoxigenic microorganisms colonize the GI tract, resulting in the diseases discussed above. It is of note that, in some cases, the enterotoxigenic microorganism is introduced into the host GI tract by ingestion of contaminated food or water.

Described herein is a method of preparing a bioactive compound delivery system. In some embodiments, the bioactive compound is arranged to be delivered to the intestine, as discussed below. Also described are pharmaceutical compositions comprising at least one bioactive compound within the delivery system. As discussed below, the delivery system comprises a matrix or lattice of at least one methacrylate polymer. The bioactive compound may be any suitable compound. In a preferred embodiment, the bioactive compound is a compound which requires a native surface structure for proper interaction with its biological target. Examples of such compounds include antibodies, bacteriophage and receptor ligands.

In one embodiment of the invention, there is provided a pharmaceutical composition comprising a solution of methacrylic acid polymers, a lyoprotectant and a bioactive compound. The pharmaceutical composition may be lyophilized.

The lyoprotectant stabilizes the bioactive compound during lyophylization. While not wishing to be bound or limited to a specific hypothesis, the inventors note that the lyoprotectant may act as an osmotic stabilizer. In view of this, compounds known in the art to act as osmotic stabilizer are suitable lyoprotectant. The lyoprotectant may be for example but by no means limited to sucrose or glucose.

In some embodiments, the bioactive agent is a bacteriophage capable of lysing at least one microorganism. In some embodiments, the bacteria is enterotoxigenic, although the pharmaceutical composition may be used to treat any suitable bacterial infection. In these embodiments, the pharmaceutical composition contains an effective amount of the bacteriophage and is administered to an animal in need of such treatment. It is of note that bacteriophage capable of lysing enterotoxigenic bacteria are well known in the art.

In other embodiments, the bioactive agent is a pharmaceutical agent, antibody, ligand or other such compound which requires a specific structure for activity. As an illustrative example, the bioactive compound may be a ligand for a specific cellular receptor and the ligand may require a specific structure or conformation to interact with the receptor. As will be appreciated by one of skill in the art, any bioactive compound known in the art for treating a specific disease or disorder may be combined with the methacrylic polymer and lyoprotectant as discussed herein to conserve the structure or conformation of the bioactive molecule such that the bioactive molecule is more effective at treating the disease or disorder. As will be appreciated by one of skill in the art, exemplary diseases and disorders are not limited to the GI tract but may be any disease or disorder wherein the therapeutic bioactive molecule or therapeutic bioactive agent requires maintenance of a specific conformation or structure for activity.

Polymeric methacrylic acid copolymers (EUDRAGITS (methacrylic acid-methyl methacrylate copolymers)) are typically applied to pharmaceutical dosage forms at a pH below that where the polymer enters solution, which is different for the various EUDRAGIT (methacrylic acid-methyl methacrylate copolymer) forms. The materials are therefore applied as a dispersion, rather than a solution. This has the benefit of creating an insoluble barrier resistant to acidic environments. It also permits the polymer to be applied in a purely aqueous environment since the eudragits are typically insoluble below a defined pH characteristic of the polymer. Polymethacrylic acid copolymers may also be applied in the protonated aqueous insoluble form by dissolution in organic solvents, in which they are soluble. This technique requires the use of organic solvents which is generally undesirable.

The present invention provides methods and compositions for preparing controlled release solid dosage forms containing viable bacteriophages. The preparations are prepared from polymethacrylic acid copolymers using mild aqueous conditions. The present invention is not limited to bacteriophages because it can be applied to preparing controlled release solid dosage forms of other complicated biologic molecules and macromolecules. These include but are by no means limited to, antibodies, receptor ligands, viruses, peptides, peptide fragments, enzymes, including digestive enzymes, DNA molecules, RNA molecules, growth factors, cytokines, bacteria and viruses, and the like.

Monolithic oral dosage formulations containing bacteriophages are made by drying bacteriophages in an aqueous solution containing the reversibly pH-dependent soluble methacrylate polymer(s) (EUDRAGITS (methacrylic acid-methyl methacrylate copolymers); FDA-approved excipients) and a lyoprotectant, for example but by no means limited to sucrose and glucose. It is of note that while not wishing to be limited to a specific hypothesis, it is believed that the lyoprotectant acts as an osmotic stabilizer. Thus, other suitable osmotic stabilizing compounds known in the art may also be used as lyoprotectants. The formulations prepared in this manner using the ingredients described contain highly viable bacteriophage that are protected from the harsh environmental conditions in the stomach. A variety of technologies, such as freeze drying and spray drying, may be used to prepare the dosage formulations. The formulations are suitable for economical end practical treatment of a variety of bacterial infections.

The ratio of polymer to lyoprotectant may vary from 200:1 to 0.1:1.

Bacteriophages can be safely encapsulated in a matrix under gentle conditions in a manner that preserves their biological activity using this method and compositions. Furthermore, the formulations release the bacteriophages upon exposure to elevated pH conditions encountered in the small intestine. As such, they represent a controlled release formulation.

These formulations have utility for the development of bacteriophage therapy for other enteric and non-enteric bacterial infections because they can be further modified using other pharmaceutical production techniques to produce other useful formulations. For example, the formulations may be further processed to make other therapeutics by encapsulation in other polymeric substances, thereby producing formulations with different drug release characteristics using means known in the art. For example, specific carriers and carrier combinations known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

In some embodiments, the above-described formulation may be combined with other compounds or compositions known in the art such that the is a pharmaceutical composition in the form of, for example, a pill, tablet, liquid, film or coating using means known in the art and as discussed below.

It is of note that the formulation discussed above may be prepared to be administered in a variety of ways, for example, topically, orally, intravenously, intramuscularly, subcutaneously, intraperitoneally, intranasally or by local or systemic intravascular infusion using means known in the art and as discussed below.

All the formulations described above can be incorporated into a variety of edible materials, such as different foods and drinks, thereby increasing their usefulness by providing vehicles of increased palatability that can be used to treat gastrointestinal tract infections in vertebrates and invertebrates. Furthermore, the formulations can be incorporated into wound dressings that can be used to treat bacterial infections at poorly vascularized locations of the body.

It is of note that the compositions as described above may be combined with permeation enhancers known in the art for improving delivery. Examples of permeation enhancers include, but are by no means limited to those compounds described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, "1975, J. Pharm. Sci. 64:901-924.

A pharmaceutical formulation that provides controlled release of bacteriophage has not been previously reported. Benefits are that it provides a formulation made using an aqueous system that does not require organic solvents. Furthermore it uses a versatile and economical production method to produce a controlled release formulation containing stable and highly potent bacteriophage. Controlled release formulations employing methacrylate polymers used in the manner described here have not been described elsewhere. The novel use is that the methacrylates are used in aqueous solution, as opposed to the more common aqueous dispersion, and that enhanced-controlled release can be achieved during a second step, namely acid treatment of dried monolithic matrix. Such acid treatment may be achieved merely by exposure to acid in an acidic environment, such as the stomach. Specifically, the acid treatment protonates the carboxyl groups in the methacrylate polymer; these groups are more protonated in dispersions, which are typically of a lower pH than a solution of the same polymeric substance. The first step of the process, drying in the presence of methacrylate in solution in the presence of lyoprotectant, provides a gentle condition under which sensitive biological agents are dried (the bacteriophage are damaged in formulation prepared with dispersions). As such, this process may also be used to make controlled release formulations of complex biological molecules that are/may be used to treat non-infectious diseases.

The invention will now be described by way of examples; however, the examples are intended to be illustrative only.

EXAMPLE 1

Preparation of Bacteriophage rV5

Bacteriophage rV5 and wV8 were propagated in broth culture using *Escherichia coli* strains sensitive to the bacteriophage according to the methods described in Sambrook and Russell (2001).

EXAMPLE 2

Preparation of Polymethacrylate Copolymer Dispersions and Solutions

EUDRAGITS (methacrylic acid-methyl methacrylate copolymers) are methacrylic acid copolymers used as excipients to control the release of active ingredients from solid pharmaceutical dosage formulations. These polymers have physiochemical properties, such as dissolution within specified pH ranges, that permit protection and entrapment of active ingredients under certain harsh environmental conditions, such as stomach. The polymers are typically used in two ways. To be exact, they are applied as thin layers from aqueous dispersions or organic solutions by spraying on cores containing drugs, or they are incorporated into monolithic forms as dry powders by direct compression techniques.

Substitution of the methacrylate polymer with varying numbers of acidic or basic groups tailor release of the active ingredient in different regions of the gastrointestinal tract. For example, EUDRAGIT (methacrylic acid-methyl methacrylate copolymer) S100 is soluble only above approximately pH 7 and it facilitates controlled release in the colon. EUDRAGIT (methacrylic acid-methyl methacrylate copolymer) L100 is soluble only above pH 6 and it facilitates controlled release in the small intestine. Generally speaking, the protonated forms of EUDRAGIT (methacrylic acid-methyl methacrylate copolymer) S100 and L100 are used in drug formulations because these forms are largely insoluble until the pH is elevated and the polymer is ionized by deprotonization. This necessitates using the polymers in one of two forms, which are as aqueous dispersions at a pH below the solution pH of the polymer, or as organic solutions in which the polymer retains it protons. Dispersion may be defined as a physiochemical system in which colloidal particles are dispersed in a continuous phase of a different composition. Conversely, solution may be defined as a uniform mixture comprised of a solvent, usually a liquid, and a solute. EUDRAGIT (methacrylic acid-methyl methacrylate copolymer) L100 and S100 are structurally similar, but differ in the degree of substitution with acidic carboxyl groups on the polymer backbone. Dispersions and solutions of EUDRAGITS (methacrylic acid-methyl methacrylate copolymers) S100 and L100 may be prepared by varying the pH of the aqueous medium in which they are placed.

A dispersion of EUDRAGIT (methacrylic acid-methyl methacrylate copolymer) L100 was made as follows:

Weigh out 110 g of EUDRAGIT (methacrylic acid-methyl methacrylate copolymer) L100 solid (Rhom Pharma) and suspend the particles in 730 ml of water.

Stir the mixture for 10 minutes at room temperature.

Add 10 N NaOH (Fisher Chemical Company) dropwise until a stable pH of approximately 5.7 is reached.

Store the material at room temperature.

The pH of the dispersion is below that required to dissolve the EUDRAGIT (methacrylic acid-methyl methacrylate copolymer) L100 polymer. The material has the appearance of a opaque white latex dispersion.

A solution of EUDRAGIT (methacrylic acid-methyl methacrylate copolymer) S100 was made as follows:

Weigh out 110 g of EUDRAGIT (methacrylic acid-methyl methacrylate copolymer) S100 solid (Rhom Pharma) and suspend the particles in 730 ml of water.

Stir the mixture for 10 minutes at room temperature.

Add 10 N NaOH (Fisher Chemical Company) dropwise until a stable pH of approximately 7.1 is reached.

Store the material at room temperature.

The pH of the dispersion is above that required to dissolve the EUDRAGIT (methacrylic acid-methyl methacrylate copolymer) S100 polymer. The material has the appearance of a clear, colorless solution.

EXAMPLE 3

Stability of rV5 in Dried Formulations Containing a) Polymethacrylate Copolymer EUDRAGIT (Methacrylic Acid-Methyl Methacrylate Copolymer) L100, b) Sucrose, and c) Polymethacrylate Copolymer EUDRAGIT (Methacrylic Acid-Methyl Methacrylate Copolymer) L100 and Sucrose Bacteriophage rV5 was added to different excipients mixtures comprised of 0-5% EUDRAGIT (methacrylic acid-methyl methacrylate copolymer) L100 dispersion and 0-3% sucrose and the resulting material was dried by lyophilization after it was frozen at −70° C. The amount of active ingredient (ie. the number of viable bacteriophage rV5) in the excipients before freezing, after freezing, and after lyophilization was determined by titrating the samples on a suitable indicator strain using methods generally known to those skilled in the art. Before the dried formulations were titrated they were solubilized with 50-100 mM carbonate/bicarbonate buffer for approximately 10 minutes.

All the excipients maintained the viability of the bacteriophage before and after freezing, indicating that they did not directly damage the bacteriophage in solution (Table 1). Zero, 2.5 and 5% sucrose maintained the viability of the rV5 after lyophilization, provided no L100 was present. EUDRAGIT (methacrylic acid-methyl methacrylate copolymer) L100 alone decreased the viability of bacteriophage rV5 by 2-3 $\log_{10}$ after lyophilization, indicating that it alone damaged the bacteriophage greatly. Importantly, 5% sucrose together with 1.5 or 3% L100 maintained the viability of the bacteriophage.

TABLE 1

Viability of rV5 in formulations containing a) polymethacrylate copolymer (Eudragit L100), b) sucrose, and c) polymethacrylate copolymer (EUDRAGIT (methacrylic acid-methyl methacrylate copolymer) L100) and sucrose.

| Formulation Component | | Bacteriophage rV5 (PFU/ml) | | |
|---|---|---|---|---|
| Sucrose | Eudragit L100 | Before Freezing | After Freezing | Reconstituted after Lyophilization |
| 0 | 0 | 2 × 10(8) | 8 × 10(8) | 4 × 10(6) |
| 0 | 0.375 | 4 × 10(7) | 1.2 × 10(8) | 6 × 10(3) |
| 0 | 0.75 | 1 × 10(8) | 2 × 10(6) | 1.2 × 10(4) |
| 0 | 1.5 | 4 × 10(7) | 1.6 × 10(7) | 1.4 × 10(4) |

TABLE 1-continued Viability of rV5 in formulations containing a) polymethacrylate copolymer (Eudragit L100), b) sucrose, and c) polymethacrylate copolymer (EUDRAGIT (methacrylic acid-methyl methacrylate copolymer) L100) and sucrose.

| Formulation Component | | Bacteriophage rV5 (PFU/ml) | | |
|---|---|---|---|---|
| Sucrose | Eudragit L100 | Before Freezing | After Freezing | Reconstituted after Lyophilization |
| 0 | 3 | $8 \times 10(7)$ | $2 \times 10(7)$ | $1.2 \times 10(4)$ |
| 2.5 | 0 | $2.6 \times 10(7)$ | $2 \times 10(8)$ | $1 \times 10(7)$ |
| 2.5 | 0.375 | $8 \times 10(7)$ | $1.2 \times 10(9)$ | $2 \times 10(4)$ |
| 2.5 | 0.75 | $2 \times 10(7)$ | $8 \times 10(7)$ | $6 \times 10(4)$ |
| 2.5 | 1.5 | $6 \times 10(7)$ | $8 \times 10(7)$ | $6 \times 10(4)$ |
| 2.5 | 3 | $1.2 \times 10(7)$ | $4 \times 10(7)$ | $4 \times 10(4)$ |
| 5 | 0 | $4 \times 10(7)$ | $4 \times 10(7)$ | $1.2 \times 10(6)$ |
| 5 | 0.375 | $8 \times 10(7)$ | $1.2 \times 10(8)$ | $4 \times 10(5)$ |
| 5 | 0.75 | $1.2 \times 10(7)$ | $1.2 \times 10(8)$ | $6 \times 10(4)$ |
| 5 | 1.5 | $6 \times 10(7)$ | $2 \times 10(7)$ | $6 \times 10(5)$ |
| 5 | 3 | $4 \times 10(7)$ | $4 \times 10(7)$ | $4 \times 10(6)$ |

These results were confirmed and extended in a related experiment. In that experiment, 0, 0.125, 2.5 and 5% sucrose maintained viability of the bacteriophage, provided the L100 was absent (Table 2). Three and 5% L100 decreased viability of the phage by 2 $\log_{10}$. Adding 2.5 or 5% sucrose to the 3 or 5% L100 maintained the viability comparable to the sucrose only samples.

Whether this combination protected the bacteriophage from the detrimental effects of acid was examined in part in Example 4.

TABLE 2

Viability of rV5 in formulations containing a) polymethacrylate copolymer (EUDRAGIT (methacrylic acid-methyl methacrylate copolymer) L100), b) sucrose, and c) polymethacrylate copolymer (EUDRAGIT (methacrylic acid-methyl methacrylate copolymer) L100) and sucrose.

| Formulation Component (initial %, w/v) | | Bacteriophage rV5 (PFU/ml) in material |
|---|---|---|
| Sucrose | Eudragit L100 | reconstituted after lyophilization |
| 0 | 0 | $8 \times 10(6)$ |
| 0 | 3 | $2 \times 10(4)$ |
| 0 | 5 | $6 \times 10(4)$ |
| 0.125 | 0 | $6 \times 10(7)$ |
| 0.125 | 3 | $1.2 \times 10(5)$ |
| 0.125 | 5 | $1.4 \times 10(4)$ |
| 2.5 | 0 | $6 \times 10(6)$ |
| 2.5 | 3 | $2 \times 10(6)$ |
| 2.5 | 5 | $1.6 \times 10(6)$ |
| 5 | 0 | $4 \times 10(7)$ |
| 5 | 3 | $4 \times 10(8)$ |
| 5 | 5 | $2 \times 10(7)$ |

EXAMPLE 4

Stability of Bacteriophage rV5 in Dried Formulations Containing Polymethacrylate Copolymer (EUDRAGIT (Methacrylic Acid-Methyl Methacrylate Copolymer) L100), Sucrose, and Polymethacrylate Copolymer (EUDRAGIT (Methacrylic Acid-Methyl Methacrylate Copolymer) L100) and Sucrose Formulations containing bacteriophage rV5 were prepared as described in Example 3 and these were left untreated or treated with 100 mM HCl for 20 minutes. The resulting acid was neutralized with bicarbonate, which also dissolved the lyophilizate, and the number of viable bacteriophage contained therein was determined as described in Example 3. As shown previously (Example 3), the formulations that contained sucrose alone and the formulations that contained sucrose and L100 maintained viability of the bacteriophage, and the formulations that contained L100 alone decreased the viability of the bacteriophage. Notably, the formulations that contained both L100 and sucrose together protected the bacteriophage from acid treatment, whereas the formulations that contained L100 or sucrose alone did not. The conclusion that can be drawn from this example is that polymethacrylic acid copolymer can protect the bacteriophage from harsh chemical conditions, but only in the presence of another agent, for example sucrose.

TABLE 3

Protection of rV5 to acid treatment for 20 minutes by formulations containing a) polymethacrylate copolymer (EUDRAGIT (methacrylic acid-methyl methacrylate copolymer) L100), b) sucrose, and c) polymethacrylate copolymer (EUDRAGIT (methacrylic acid-methyl methacrylate copolymer) L100) and sucrose.

| Formulation Component (initial %, w/v) | | Bacteriophage rV5 (PFU/ml) in lyophilized material reconstituted |
|---|---|---|
| Sucrose | Eudragit L100 | after 20 min acid treatment |
| 0 | 0 | none detected |
| 0 | 3 | none detected |
| 0 | 5 | none detected |
| 0.125 | 0 | $1 \times 10(3)$ |
| 0.125 | 3 | $1 \times 10(3)$ |
| 0.125 | 5 | $3 \times 10(4)$ |
| 2.5 | 0 | $1.5 \times 10(4)$ |
| 2.5 | 3 | $3 \times 10(4)$ |
| 2.5 | 5 | $1 \times 10(5)$ |
| 5 | 0 | $2.5 \times 10(4)$ |
| 5 | 3 | $2 \times 10(7)$ |
| 5 | 5 | $25 \times 10(6)$ |

In a related experiment these results were confirmed and extended. In that experiment, formulations containing bacteriophage rV5 and 0, 2.5, and 5% sucrose and 0, 3 and 5% L100 were treated overnight with 100 mM HCl and then neutralized and solubilized with bicarbonate buffer and titrated as described above to determine the number of viable bacteriophage remaining. Significantly, only the formulation containing sucrose and L100 afforded protection to the bacteriophage following overnight exposure to acidic conditions (Table 4).

TABLE 4

Protection of rV5 to acid treatment overnight by
formulations containing a) polymethacrylate copolymer
(EUDRAGIT (methacrylic acid-methyl methacrylate copolymer)
L100), b) sucrose, and c) polymethacrylate
copolymer (EUDRAGIT (methacrylic acid-methyl
methacrylate copolymer) L100) and sucrose.

| Formulation | | Viability of Bacteriophage (PFU/ml) | |
|---|---|---|---|
| Eudragit L100 (%), before drying | Sucrose (%, before drying) | Reconstituted without acid treatment | Reconstituted after overnight acid treatment |
| 0 | 2.5 | 1.5 × 10(6) | None |
| 3 | 2.5 | 1 × 10(6) | None |
| 5 | 2.5 | 3.5 × 10(5) | 5 × 10(5) |
| 0 | 5 | 3 × 10(6) | None |
| 3 | 5 | 2 × 10(6) | None |
| 5 | 5 | 5.5 × 10(5) | 5 × 10(4) |

Whether this combination of materials entrapped the bacteriophage, or merely protected it in solution was examined in experiments described in Example 5.

EXAMPLE 5

Retention of Bacteriophage in Acidic Environments by Formulations Containing Sucrose and S100

Dried formulations containing bacteriophage rV5 or wV8, 5% sucrose and 5-10% S100 were prepared according to Example 3 with S100 solution prepared according to Example 2. These materials were treated sequentially four times over a period of approximately 15 minutes with 100 mM HCl. At the end of each treatment, the acid was removed, neutralized with bicarbonate buffer, then viable bacteriophage in the samples were titrated according to Example 3. Furthermore, the formulation remaining at the end of the treatments was dissolved in bicarbonate buffer, and then the number of viable bacteriophage in it was also determined by titration as described in Example 3. No bacteriophages were liberated by the acid treatments and bacteriophage remained in the formulations after the acid treatments (Table 5, 6).

TABLE 5

Controlled release of bacteriophage rV5 from formulation
made using excipient containing 5% sucrose and 10%
polymethacrylate S100.

| Sample | Bacteriophage content in sample | |
|---|---|---|
| | rV5 | wV8 |
| Original formulation before acid treatment | 8 × 10(8) | 1.5 × 10(7) |
| Supernatant from acid treatment 1 | None | none |
| Supernatant from acid treatment 1 | None | none |
| Supernatant from acid treatment 1 | None | none |
| Supernatant from acid treatment 1 | None | none |
| Remaining in formulation after acid treatment | 2.5 × 10(8) PFU | 3.0 × 10(7) |

TABLE 6

Controlled release of bacteriophage rV5 from formulation
made using excipient containing 5% sucrose and 5%
polymethacrylate S100.

| Sample | Bacteriophage content in Sample | |
|---|---|---|
| | RV5 | wV8 |
| Original formulation before acid treatment | 3.0 × 10(8) | 1.5 × 10(8) |
| Supernatant from acid treatment 1 | None | none |
| Supernatant from acid treatment 1 | None | none |
| Supernatant from acid treatment 1 | None | none |
| Supernatant from acid treatment 1 | None | none |
| Remaining in formulation after acid treatment | 7.5 × 10(6) PFU | 6.5 × 10(7) |

A further experiment was conducted with formulations containing rV5 and wV8, S100 and sucrose as described above to further examine the ability of the matrix to protect the bacteriophages. In that experiment, the formulations were exposed to acid for 20, 60, 120 minutes and overnight, and then the viable bacteriophage remaining was determined. Each matrix prevented inactivation of bacteriophages rV5 and wV8 during the overnight incubation with acid (Table 7).

TABLE 7

Controlled release of bacteriophage rV5 and wV8 from
formulations containing polymethacrylate copolymer
(EUDRAGIT (methacrylic acid-methyl methacrylate
copolymer) S100) and sucrose.

| Time of Acid Treatment | Viability of Bacteriophage in Formulation of Different Compositions (PFU/ml) | | | |
|---|---|---|---|---|
| | 5% sucrose + 5% S100 | | 5% sucrose + 10% S100 | |
| | rV5 | wV8 | rV5 | wV8 |
| 0 minutes | 3 × 10(8) | 1.5 × 10(8) | 8 × 10(8) | 1.5 × 10(7) |
| 20 minutes | 3 × 10(7) | 5.5 × 10(7) | 1.5 × 10(6) | 2.5 × 10(7) |
| 60 minutes | 1 × 10(7) | 1 × 10(6) | 1 × 10(7) | 1 × 10(6) |
| 120 minutes | 5 × 10(7) | 1.5 × 10(6) | 7.5 × 10(7) | 1 × 10(7) |
| Overnight | 7 × 10(6) | 1 × 10(5) | 1 × 10(7) | 1 × 10(5) |

Furthermore, an experiment was conducted to examine release of bacteriophages rV5 and wV8 under mildly basic conditions. Dried formulations containing bacteriophage rV5 or wV8, 5% sucrose and 5-10% S100 were prepared according to Example 3 with S100 solution prepared according to Example 2. These materials were incubated with 10 mM phosphate buffered saline (pH 7.2) for 20, 60, 120 minutes and overnight, then centrifuged at 13,000×g, and then viable bacteriophage in the supernatant of the samples were titrated according to Example 3. Both rV5 and wV8 were rapidly released by the matrices in 20 minutes (Table 8).

TABLE 8

Rapid release of rV5 and wV8 from formulations containing polymethacrylate copolymer (EUDRAGIT (methacrylic acid-methyl methacrylate copolymer) S100) and sucrose.

| Time of PBS Treatment | Release of Bacteriophage by Formulations of Different Compositions (PFU/ml) | | | |
|---|---|---|---|---|
| | 5% sucrose + 5% S100 | | 5% sucrose + 10% S100 | |
| | rV5 | wV8 | rV5 | wV8 |
| 0 minutes (dissolved in bicarbonate buffer, pH 9.6) | $5 \times 10(7)$ | $1.5 \times 10(8)$ | $1.5 \times 10(7)$ | $1 \times 10(7)$ |
| 20 minutes | $1 \times 10(8)$ | $5 \times 10(6)$ | $5 \times 10(7)$ | $3 \times 10(7)$ |
| 60 minutes | $2 \times 10(8)$ | $2 \times 10(7)$ | $2.5 \times 10(8)$ | $3.5 \times 10(7)$ |
| 120 minutes | $5 \times 10(7)$ | $5 \times 10(7)$ | $1.5 \times 10(7)$ | $1 \times 10(8)$ |
| Overnight | $5 \times 10(7)$ | $4.5 \times 10(8)$ | $1 \times 10(8)$ | $1 \times 10(8)$ |

These results show that formulations prepared in the manner of Example 3 using solutions of polymethacrylate copolymer trap macromolecular biological material and protect it from acidic environments. Furthermore the formulations prepared in the manner of Example 3 release the macromolecular material upon exposure to conditions that will result in dissolution of the entrapping polymer.

EXAMPLE 7

Spray Drying Bacteriophage in Polymethacrylate Copolymer Solution (EUDRAGIT (Methacrylic Acid-Methyl Methacrylate Copolymer) S100) Containing Sucrose Liquid intermediaries containing bacteriophage rV5 were prepared containing 1.25, 2.5, and 5% sucrose and 2.5, 5, and 10% EUDRAGIT (methacrylic acid-methyl methacrylate copolymer) S100, prepared as a solution according to Example 2 and then spray dried using an inlet temperature 135 C and an outlet temperature 108 C. The viability of bacteriophage in the resulting dried powder formulations, and the initial aqueous intermediary were determined as described in Example 3. Bacteriophage spray dried in all the excipients remained viable (Table 8).

TABLE 9

Viability of bacteriophage rV5 in formulations containing polymethacrylate copolymer (EUDRAGIT (methacrylic acid-methyl methacrylate copolymer) S100) and sucrose prepared by spray drying.

| Formulation | Bacteriophage Viability (PFU/ml) | |
|---|---|---|
| | Before Spray Drying | After Spray Drying |
| 2.5% S100, 1.25% sucrose | $3.5 \times 10(8)$ | $4.1 \times 10(7)$ |
| 5% S100, 2.5% sucrose | $3.5 \times 10(8)$ | $1.5 \times 10(7)$ |
| 10% S100, 5% sucrose | $5 \times 10(8)$ | $6.7 \times 10(6)$ |

While the preferred embodiments of the invention have been described above, it will be recognized and understood that various modifications may be made therein, and the appended claims are intended to cover all such modifications which may fall within the spirit and scope of the invention.

The invention claimed is:

1. A pharmaceutical composition containing viable bacteriophages prepared by drying bacteriophages in an aqueous solution containing a methacrylate polymer and a stabilizer selected from glucose and sucrose.

2. The pharmaceutical composition according to claim 1 wherein the composition is dried by freeze-drying.

3. The pharmaceutical composition according to claim 1 wherein the methacrylate polymer is a methacrylic acid-methyl methacrylate copolymer.

4. The pharmaceutical composition according to claim 1 wherein the composition is dried by spray drying.

5. The pharmaceutical composition according to claim 1 wherein mild aqueous conditions are used during preparation of the pharmaceutical composition.

6. The pharmaceutical composition according to claim 1 wherein the pharmaceutical composition is in a solid dosage form.

7. The pharmaceutical composition according to claim 1 wherein the pharmaceutical composition is prepared in an aqueous system that does not require organic solvents.

* * * * *